United States Patent
Nolan et al.

(10) Patent No.: US 10,857,016 B2
(45) Date of Patent: Dec. 8, 2020

(54) PROXIMAL AND DISTAL RELEASE DELIVERY SYSTEM

(71) Applicant: BOSTON SCIENTIFIC SCIMED, INC., Maple Grove, MN (US)

(72) Inventors: Damien V. Nolan, Galway (IE);
Geraldine A. Toner, Raphoe (IE);
Matthew Montague, Galway (IE);
Enda Connaughton, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 66 days.

(21) Appl. No.: 15/962,800

(22) Filed: Apr. 25, 2018

(65) Prior Publication Data

US 2018/0311061 A1    Nov. 1, 2018

Related U.S. Application Data

(60) Provisional application No. 62/490,539, filed on Apr. 26, 2017.

(51) Int. Cl.
*A61F 2/966* (2013.01)
*A61F 2/82* (2013.01)
*A61F 2/95* (2013.01)

(52) U.S. Cl.
CPC .......... *A61F 2/966* (2013.01); *A61F 2/82* (2013.01); *A61F 2002/9517* (2013.01); *A61F 2002/9665* (2013.01)

(58) Field of Classification Search
CPC .......... A61F 2/2433; A61F 2/966; A61F 2/95; A61F 2/82; A61F 2/9534; A61F 2/9517;
(Continued)

(56) References Cited

U.S. PATENT DOCUMENTS 5,078,720 A    1/1992    Burton et al.
5,201,757 A    4/1993    Heyn et al.
(Continued)

FOREIGN PATENT DOCUMENTS

JP    2010527695 A    8/2010
WO    9526775 A1    10/1995
(Continued)

OTHER PUBLICATIONS

International Search Report and Written Opinion dated Jun. 27, 2018 for International Application No. PCT/US2018/029427.

*Primary Examiner* — Tan-Uyen T Ho
*Assistant Examiner* — Lee O Chedister
(74) *Attorney, Agent, or Firm* — Seager, Tufte & Wickhem, LLP

(57) ABSTRACT

Stent delivery device includes an inner member having a distal tip, a stent disposed over a stent receiving region of the inner member, an outer sheath slidable over the inner member, a stent sheath removably coupled to both the distal tip and a distal end of the outer sheath, and a stent expanding element attached to the distal tip and/or the distal end of the outer sheath. The stent expanding element is biased in an elevated position and aids expansion of the stent when the stent sheath is removed. The stent delivery device includes a proximal junction removably coupling the distal end of the outer sheath to the stent sheath, and a proximal junction removably coupling the stent sheath to the distal tip. Each of the proximal and distal junctions are separately actuatable to decouple the stent sheath from either the distal tip or the outer sheath.

20 Claims, 15 Drawing Sheets

(58) Field of Classification Search
CPC .............. A61F 2/2427; A61B 18/1492; Y10T 292/1051; Y10T 292/61
USPC .......................................... 606/41; 604/106
See application file for complete search history.

(56) References Cited

U.S. PATENT DOCUMENTS

| | | | |
|---|---|---|---|
| 5,242,399 A | 9/1993 | Lau et al. | |
| 5,275,622 A | 1/1994 | Lazarus et al. | |
| 5,415,664 A | 5/1995 | Pinchuk | |
| 5,443,477 A * | 8/1995 | Marin | A61F 2/95 604/106 |
| 5,445,646 A | 8/1995 | Euteneuer et al. | |
| 5,534,007 A | 7/1996 | Germain et al. | |
| 5,603,698 A | 2/1997 | Roberts et al. | |
| 5,902,333 A | 5/1999 | Roberts et al. | |
| 5,980,533 A | 11/1999 | Holman | |
| 6,241,758 B1 | 6/2001 | Cox | |
| 6,582,460 B1 | 6/2003 | Cryer | |
| 6,849,084 B2 | 2/2005 | Rabkin et al. | |
| 6,994,721 B2 | 2/2006 | Israel | |
| 7,004,964 B2 | 2/2006 | Thompson et al. | |
| 7,074,236 B2 | 7/2006 | Rabkin et al. | |
| 7,235,095 B2 | 6/2007 | Haverkost et al. | |
| 7,331,985 B2 | 2/2008 | Thompson et al. | |
| 7,887,573 B2 | 2/2011 | Haverkost et al. | |
| 8,048,148 B2 | 11/2011 | Viller | |
| 8,518,098 B2 | 8/2013 | Roeder et al. | |
| 8,747,459 B2 | 6/2014 | Nguyen et al. | |
| 8,864,811 B2 | 10/2014 | Kao | |
| 9,101,507 B2 | 8/2015 | Caselnova | |
| 9,295,550 B2 | 3/2016 | Nguyen et al. | |
| 9,301,864 B2 * | 4/2016 | Kao | A61F 2/966 |
| 9,314,360 B2 | 4/2016 | Kao | |
| 9,339,384 B2 * | 5/2016 | Tran | A61F 2/2433 |
| 2003/0163189 A1 | 8/2003 | Thompson et al. | |
| 2004/0127912 A1 | 7/2004 | Rabkin et al. | |
| 2005/0288764 A1 | 12/2005 | Snow et al. | |
| 2006/0136036 A1 | 6/2006 | Thompson et al. | |
| 2006/0142837 A1 | 6/2006 | Haverkost et al. | |
| 2007/0233222 A1 | 10/2007 | Roeder et al. | |
| 2008/0294230 A1 | 11/2008 | Parker | |
| 2009/0264978 A1 | 10/2009 | Dieck et al. | |
| 2011/0307049 A1 | 12/2011 | Kao | |
| 2013/0110106 A1 * | 5/2013 | Richardson | A61B 18/1492 606/41 |
| 2018/0000620 A1 | 1/2018 | Folan et al. | |

FOREIGN PATENT DOCUMENTS

| | | |
|---|---|---|
| WO | 03051425 A2 | 6/2003 |
| WO | 2008147602 A2 | 12/2008 |
| WO | 2018005628 A1 | 1/2018 |

* cited by examiner

PROXIMAL AND DISTAL RELEASE DELIVERY SYSTEM

CROSS REFERENCE TO RELATED APPLICATIONS

The present application claims the benefit of and priority to U.S. Provisional Patent Application Ser. No. 62/490,539, filed Apr. 26, 2017, the disclosure of which is incorporated herein by reference.

TECHNICAL FIELD

The disclosure is directed to devices for delivering expandable stents. More particularly, the disclosure is directed to a device that selectively deploys a stent in a distal to proximal or a proximal to distal manner.

BACKGROUND

Delivery devices for expandable stents, such as those used in endoscopic applications, generally have an outer sheath that retracts to allow the stent to be expanded radially at the target site. Retraction of the outer sheath in the proximal direction exposes the stent in a distal to proximal direction, thus allows the distal end of the stent to be expanded first, providing a distal-to-proximal direction of expansion. This manner of deployment may allow the distal end of the stent to be placed in a particular location. However, the final location of the proximal end of the stent may not be known until the stent is fully expanded, particularly when the stent is self-expanding. When a specific location of the proximal end of the stent is desired, deploying the stent in a distal-to-proximal manner may require estimation of where the proximal end will reside upon complete expansion of the stent. Such an estimation may not have the desired precision needed for proper placement of the stent. There is an ongoing need to provide alternative delivery devices to selectively deploy stents in either a distal-to-proximal or proximal-to-distal manner.

BRIEF SUMMARY

This disclosure provides design, material, and use alternatives for medical devices, including delivery systems.

A first example includes a stent delivery system. The system includes an elongated inner member extending between a distal tip and a proximal end, a stent surrounding a stent receiving region of the elongated inner member, the stent having a collapsed configuration and an expanded configuration. The system also includes an elongated outer sheath slidably disposed over the inner member, the outer sheath extending between a distal end and a proximal end, a stent sheath surrounding the stent to restrain the stent in the collapsed configuration, a proximal junction detachably coupling the distal end of the outer sheath to a proximal end of the stent sheath, the proximal junction being actuatable to selectively uncouple the distal end of the outer sheath from the proximal end of the stent sheath, and a distal junction detachably coupling a distal end of the stent sheath to the distal tip of the inner member, the distal junction being actuatable to selectively uncouple the stent sheath from the distal tip. The proximal junction is actuatable by rotating the inner member relative to the outer sheath in a first direction, and the distal junction is actuatable by rotating the inner member relative to the outer sheath in a second direction that is opposite the first direction, and at least a first stent expanding element disposed at at least one of the distal tip or the distal end of the outer sheath, the first stent expanding element having a radially retracted position and a radially elevated position.

Alternatively or additionally to any of the above examples, the distal tip includes a proximally extending threaded element, the distal end of the outer sheath includes a distally extending threaded element, and the stent sheath includes threaded cavities on the distal and proximal ends thereof, the threaded cavities configured to receive the proximally and distally extending threaded elements.

Alternatively or additionally to any of the above examples, the distally and proximally extending threaded elements are tapered.

Alternatively or additionally to any of the above examples, the distal and proximal threaded connections are each fully coupled and uncoupled by less than a 360 degree turn.

Alternatively or additionally to any of the above examples, the first stent expanding element includes a first elongated member having a first end attached to the proximally extending threaded element on the distal tip or to the distally extending threaded element on the distal end of the outer sheath, the first stent expanding element having a second free end opposite the first end.

Alternatively or additionally to any of the above examples, the stent delivery system further includes a first spring biasing the first stent expanding element in the elevated position.

Alternatively or additionally to any of the above examples, the first spring is disposed in a first groove extending longitudinally through the threading on the threaded element to which the first elongated member is attached, wherein the first elongated member is disposed within the first groove when the first stent expanding element is in the retracted position.

Alternatively or additionally to any of the above examples, the stent delivery system further includes a first slider element extending from a proximal region of the outer sheath to a distal end positioned adjacent the first end of the first elongated member, the first slider element configured to slide over a portion of the first elongated member, moving the first stent expanding element from the elevated position to the retracted position.

Alternatively or additionally to any of the above examples, the first stent expanding element is disposed on the distal tip, the system further comprising a second stent expanding element disposed on the distal end of the outer sheath.

Alternatively or additionally to any of the above examples, the first stent expanding element has a free end extending proximally and the second stent expanding element has a free end extending distally.

Alternatively or additionally to any of the above examples, the first stent expanding element is disposed on the distal tip, and the system further includes a second stent expanding element disposed at the distal end of the outer sheath, the second stent expanding element including a second elongated member having a first end attached to the distally extending threaded element on the distal end of the outer sheath and a second free end opposite its first end, the second stent expanding element having a radially retracted position and a radially elevated position, and a second slider element extending from a proximal region of the outer sheath to a distal end positioned adjacent the first end of the second elongated member, the second slider element configured to slide over a portion of the second elongated member, moving the second stent expanding element from the elevated position to the retracted position.

Alternatively or additionally to any of the above examples, the first and second sliders are independently moveable.

Alternatively or additionally to any of the above examples, the stent is deployable in a proximal-to-distal manner by uncoupling the proximal junction and moving the distal tip and stent sheath distally together relative to the stent.

Alternatively or additionally to any of the above examples, the stent is deployable in a distal-to-proximal manner by uncoupling the distal junction and moving the stent sheath and outer sheath proximally together relative to the stent.

Another example is a method of selectively deploying a stent in a proximal-to-distal manner or in a distal-to-proximal manner, including advancing a stent delivery system to a target location, the stent delivery system including an elongated inner member extending between a distal tip and a proximal end, a stent surrounding a stent receiving region of the elongated inner member and having a collapsed configuration and an expanded configuration, an elongated outer sheath slidably disposed over the inner member and extending between a distal end and a proximal end, a stent sheath surrounding the stent and removably coupled to the distal tip of the inner member and the distal end of the outer sheath, a first stent expanding element disposed at the distal tip, and a second stent expanding element disposed at the distal end of the outer sheath, the first and second stent expanding elements having a retracted position and an elevated position, the first and second stent expanding elements being biased in the elevated position. The method further includes deploying the stent in a distal-to-proximal manner by rotating the inner member relative to the outer sheath in a first rotational direction, to selectively decouple a distal end of the stent sheath from the distal tip, and moving the stent sheath coupled to the outer sheath proximally relative to the stent to uncover the stent, wherein moving the stent sheath proximally away from the distal tip causes the first stent expanding element to return to the biased elevated position and hold the stent as the stent sheath is moved proximally away from the stent. Alternatively the method includes deploying the stent in a proximal-to-distal manner by rotating the inner member relative to the outer sheath in a second rotational direction opposite the first rotational direction to selectively decouple the distal end of the outer sheath from a proximal end of the stent sheath, and moving the stent sheath coupled to the distal tip distally relative to the stent to uncover the stent, wherein moving the stent sheath distally away from the distal end of the outer sheath causes the second stent expanding element to return to the biased elevated position and hold the stent as the stent sheath is moved distally away from the stent.

Another example is a stent delivery system including an elongated inner member extending between a distal tip and a proximal end, a stent surrounding a stent receiving region of the elongated inner member, the stent having a collapsed configuration and an expanded configuration, an elongated outer sheath slidably disposed over the inner member, the outer sheath extending between a distal end and a proximal end, a stent sheath surrounding the stent to restrain the stent in the collapsed configuration. The system also includes a proximal junction detachably coupling the distal end of the outer sheath to a proximal end of the stent sheath, the proximal junction being actuatable to selectively uncouple the distal end of the outer sheath from the proximal end of the stent sheath, and a distal junction detachably coupling a distal end of the stent sheath to the distal tip of the inner member, the distal junction being actuatable to selectively uncouple the stent sheath from the distal tip. The proximal junction is actuatable by rotating the inner member relative to the outer sheath in a first direction, and the distal junction is actuatable by rotating the inner member relative to the outer sheath in a second direction that is opposite the first direction, and a first stent expanding element disposed at the distal tip and a second stent expanding element disposed at the distal end of the outer sheath, the first and second stent expanding elements each having a radially retracted position and a radially elevated position, wherein the first stent expanding element includes a first elongated member having a first end attached to the distal tip and a second free end, and the second stent expanding element includes a second elongated member having a first end attached to the distal end of the outer sheath and a second free end, wherein the first and second stent expanding elements are each biased in the elevated position.

Alternatively or additionally to any of the above examples, the stent delivery system further includes a first spring disposed in a first groove extending longitudinally through threading on a threaded element extending proximally from the distal tip, the first spring disposed under the first end of the first elongated member and biasing the first elongated member in the elevated position, wherein the first elongated member is disposed within the first groove when the first stent expanding element is in the retracted position, and a second spring disposed in a second groove extending longitudinally through threading on a threaded element extending distally from the distal end of the outer sheath, the second spring disposed under the first end of the second elongated member and biasing the second elongated member in the elevated position, wherein the second elongated member is disposed within the second groove when the second stent expanding element is in the retracted position.

Alternatively or additionally to any of the above examples, the stent delivery system further includes a first slider element extending from a proximal region of the outer sheath to a distal end positioned adjacent the first end of the first elongated member, the first slider element configured to slide over a portion of the first elongated member, moving the first stent expanding element from the elevated position to the retracted position, and a second slider element extending from a proximal region of the outer sheath to a distal end positioned adjacent the first end of the second elongated member, the second slider element configured to slide over a portion of the second elongated member, moving the second stent expanding element from the elevated position to the retracted position.

Alternatively or additionally to any of the above examples, the first and second sliders are independently moveable.

Alternatively or additionally to any of the above examples, the distal tip includes a proximally extending threaded element, the distal end of the outer sheath includes a distally extending threaded element, and the stent sheath includes threaded cavities on the distal and proximal ends thereof, the threaded cavities configured to receive the proximally and distally extending threaded elements, wherein the proximally and distally extending threaded elements are each tapered.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

Figure 1:
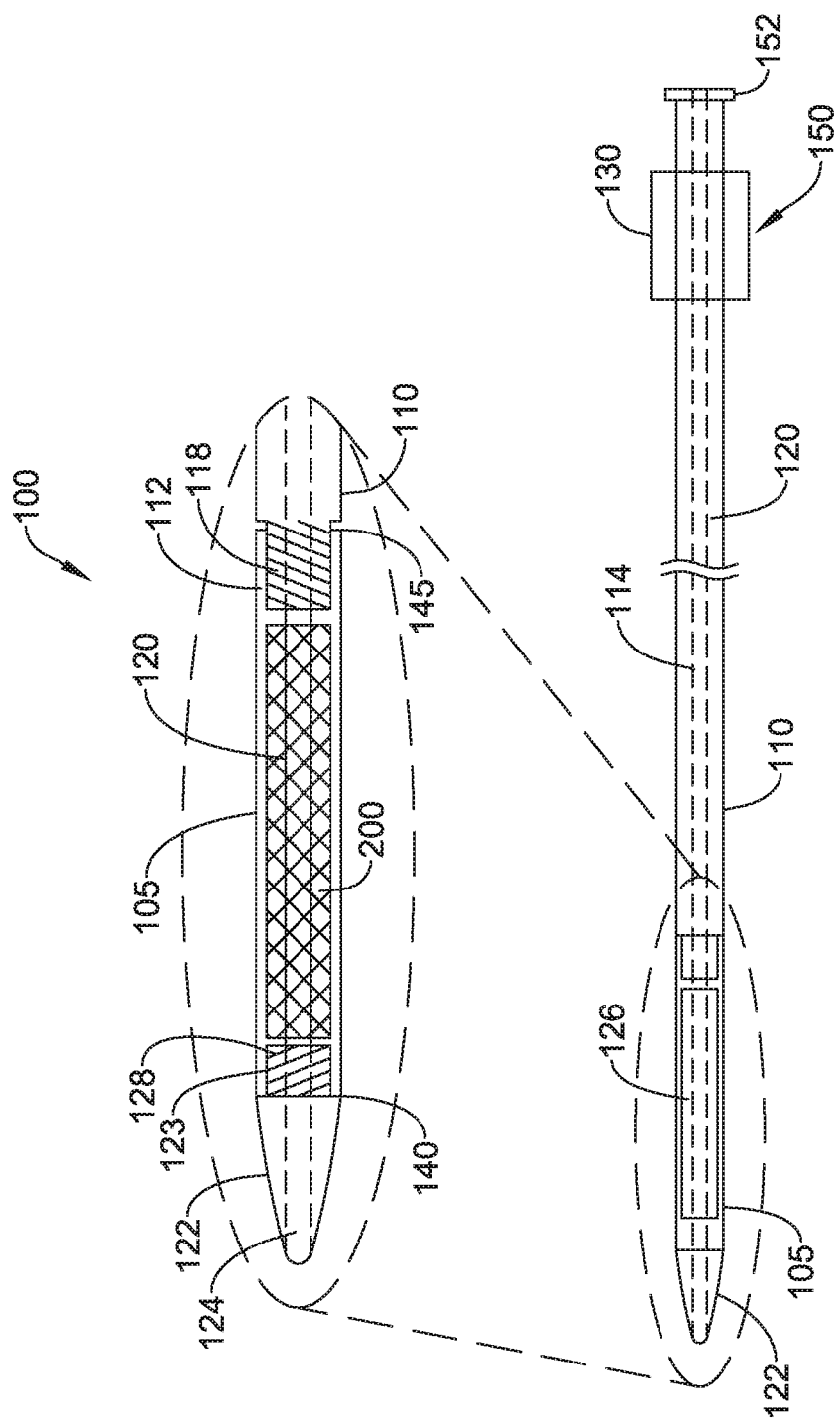
FIG. 1 is a side view of a stent delivery system in accordance with an embodiment of the disclosure, including an enlarged view of the distal portion thereof.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification. Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure. The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications may be disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

It is noted that references in the specification to "an embodiment", "an example", "some embodiments", "some examples", "another embodiment", "another example" etc., indicate that the embodiment or example described may include one or more particular features, structures, and/or characteristics. However, such recitations do not necessarily mean that all embodiments or examples include the particular features, structures, and/or characteristics. Additionally, when particular features, structures, and/or characteristics are described in connection with one embodiment or example, it should be understood that such features, structures, and/or characteristics may also be used connection with other embodiments and examples whether or not explicitly described unless clearly stated to the contrary.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 illustrates a stent delivery device 100 that includes an outer sheath 110, a stent sheath 105, and an inner member 120 extending through and longitudinally slidable within the stent sheath 105 and the outer sheath 110. The inner member 120 may include a distal tip 122 fixed to the distal end thereof. The outer sheath 110 may cover the majority of the device 100 excluding a portion of the distal end of the device 100 including the stent sheath 105 and the distal tip 122. The outer sheath 110 may be characterized by a flexible tube which includes one or more lumens 114 extending therethrough. The proximal ends of the outer sheath 110 and inner member 120 may be attached, or otherwise coupled to components of a handle assembly 150.

The inner member 120 may be a flexible tube extending through the lumen 114 of the outer sheath 110, and through the hollow tubular stent sheath 105. Guidance elements such as pull wires (not shown) may be disposed with the lumen 114, or one or more additional lumens to help navigate the delivery device 100 and/or actuate one or more components of the delivery device 100. The device 100 may be sized and configured for use in a range of medical applications, including, but not limited to, vascular applications or gastrointestinal applications, such as biliary, esophageal or colonic applications.

A proximal end of the inner member 120 may be fixedly attached, or otherwise coupled to a handle 130 of the handle assembly 150. The inner member 120 may include a tubular portion extending between a proximal knob 152 and the distal tip 122, with the tubular portion extending through the lumen 114 of the outer sheath 110 and through the stent sheath 105. The inner member 120 may include at least one lumen 124, such as a guidewire lumen, extending therethrough. For example, lumen 124 may extend through the entire length of the inner member 120 and tip 122. In some instances, the stent delivery device 100 may be routed over a guidewire (not shown), which may be received through the lumen 124.

The stent sheath 105 may be positioned longitudinally between the outer sheath 110 and the distal tip 122. For example, the stent sheath 105 may be removably connected to the distal end 112 of the outer sheath 110 at a proximal junction 145 and removably connected to the proximal end 123 of the distal tip 122 at a distal junction 140, as illustrated in FIG. 1. The removable connection between the stent sheath 105 and the outer sheath 110 and the distal tip 122 may be a threaded connection, for example. In order to allow the proximal junction 145 and distal junction 140 to be separately and independently released, the threading of the connections may be reversed. For example, the distal junction 140 may have right hand threading 128 and the proximal junction 145 may have left hand threading 118. In such a configuration, the distal junction 140 may be released by rotating the inner member 120 (and thus the distal tip 122) via the handle 130 to the right or clockwise relative to the outer sheath 110 and the stent sheath 105. The proximal junction 145 may be released by rotating the outer sheath 110 to the right or clockwise relative to the inner member handle 130, the stent sheath 105, the inner member 120, and the distal tip 122. The outer sheath 110 may be grasped directly at a proximal end thereof and the inner member 120 may be rotated by grasping and rotating the knob 152 or handle 130. Alternatively, the distal junction 140 may have left hand threading 128 and the proximal junction 145 may have right hand threading 118. In such a configuration, the direct of relative rotation between the components may be reversed. The oppositely threaded distal and proximal junctions 140, 145 allow only one end of the stent sheath 105 (i.e., only one of the junctions) to be disconnected at a time, thus providing either distal-first (i.e., distal-to-proximal) or proximal-first (i.e., proximal-to-distal) delivery of the stent. In other words, the stent sheath 105 will remain connected to either the inner member 120 (via the distal tip 122) or the outer sheath 110, depending on which junction is separated.

Figure 2:
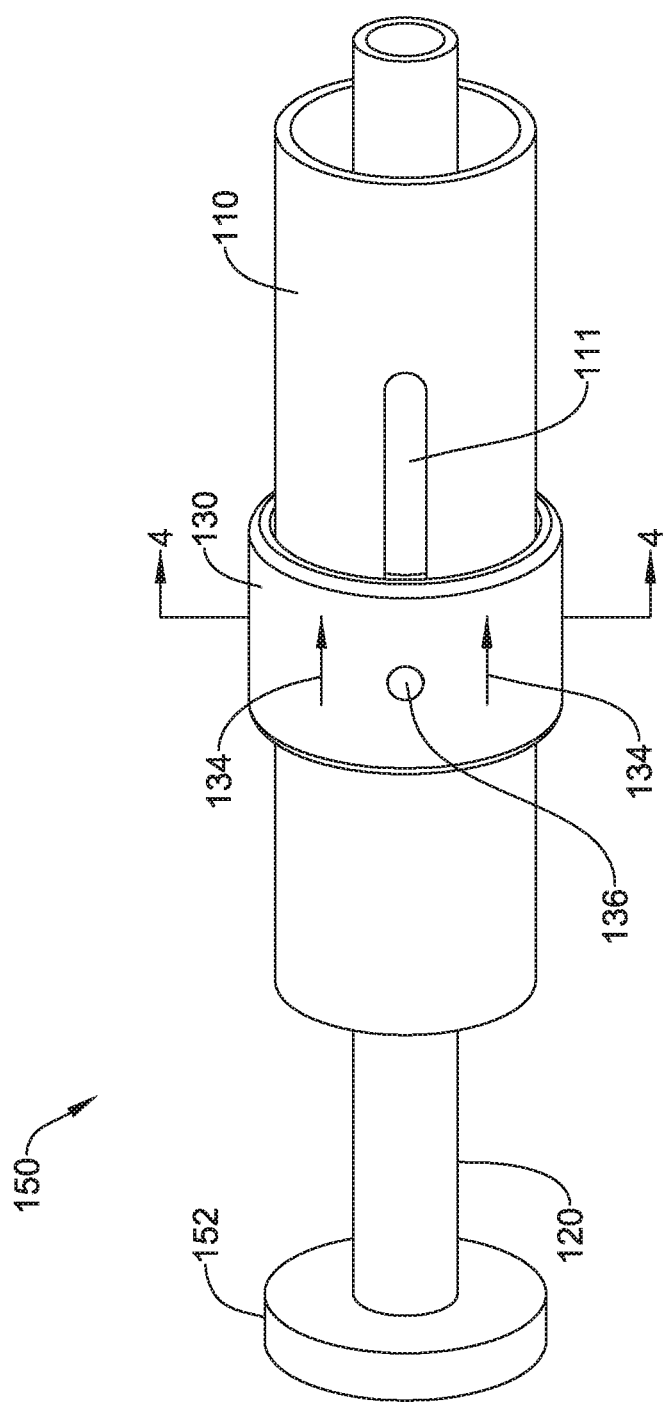
FIG. 2 is a perspective view of the proximal end of the system showing one embodiment of a handle assembly.

In some instances, the handle assembly 150 may include a knob 152 disposed on the proximal end of the inner member 120, as shown in FIG. 2. Rotation of the knob 152 rotates the inner member 120 relative to the outer sheath 110. Rotation may be provided by a circumferential slot 115 in the outer sheath 110, as shown in FIG. 3 and discussed below.

Figure 3:
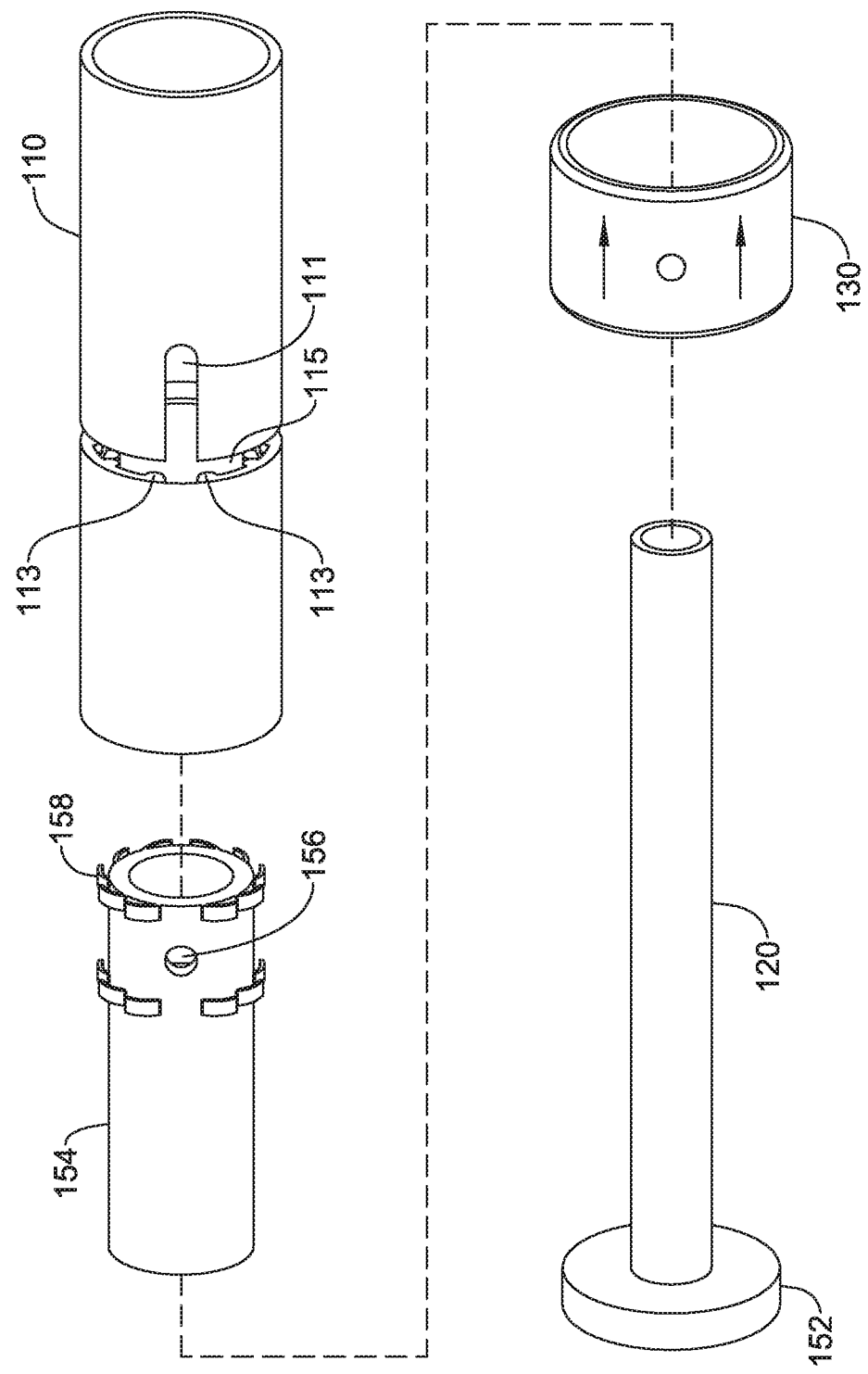
FIG. 3 is an exploded perspective view of the handle assembly of FIG. 2.

The elements of one example of a handle assembly 150 are shown in FIG. 3 and include a coupler 154 disposed inside the outer sheath 110 and the handle 130 disposed around the outside of the outer sheath 110. The handle 130 may have a pin 132 (see FIG. 4) extending inward. The pin 132 may extend through the circumferential slot 115 in the outer sheath 110, through an opening 156 in the wall of the coupler 154 and be fixedly attached to the inner member 120. The inner member 120, coupler 154, and handle 130 are moveable together both rotationally and axially. The user may rotate the inner member 120 relative to the outer sheath 110 by rotating either the handle 130 or the knob 152 on the proximal end of the inner member 120. The pin 132 travels around the circumferential slot 115 as the handle 130 rotates. The circumferential slot 115 is connected to and in communication with the longitudinal channel 111. The inner member 120 may be slid axially within the outer sheath 110 by moving either the handle 130 or the knob 152. The pin 132 travels along the longitudinal channel 111 as the handle 130 moves axially relative to the outer sheath 110.

Figure 4:
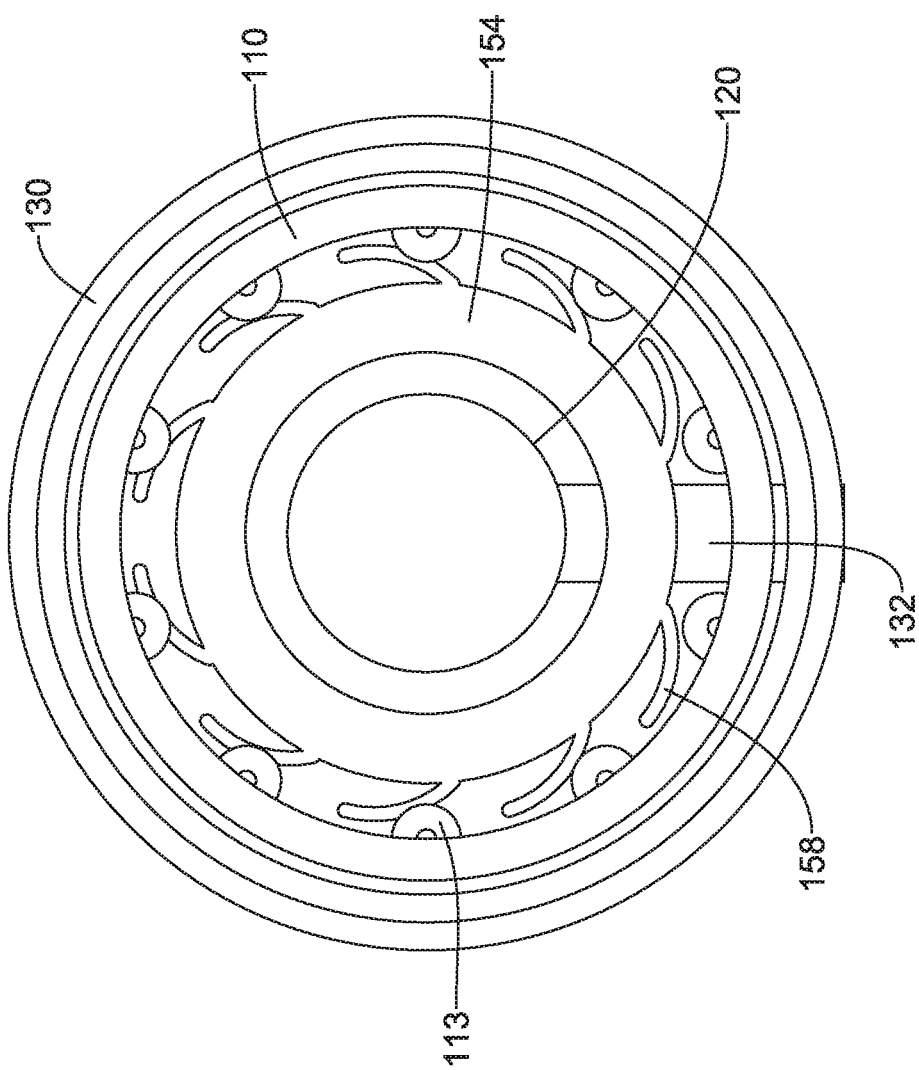
FIG. 4 is a cross-sectional view of the handle assembly taken along lines 4-4 of FIG. 2.

The coupler 154 may have a plurality of finger-like projections 158 extending outward from the outer surface. In some examples, the projections 158 disposed around a first half of the circumference of the coupler 154 are curved in a first direction and the projections 158 disposed around the second half of the circumference are curved in a second direction opposite the first direction, as shown in FIGS. 3 and 4. The coupler 154 may have at least one set of opposing projections 158. In the example shown in FIG. 3, the coupler 154 has two sets of opposing projections 158, spaced apart along the longitudinal axis of the coupler 154. The projections 158 slide along the inner surface of the outer sheath 110 when the coupler 154 is rotated relative to the outer sheath 110. The projections 158 may allow the coupler 154 and attached inner member 120 to rotate relative to the outer sheath 110 while maintaining the radial position of the inner member 120 and coupler 154 within the outer sheath 110.

Figure 5:
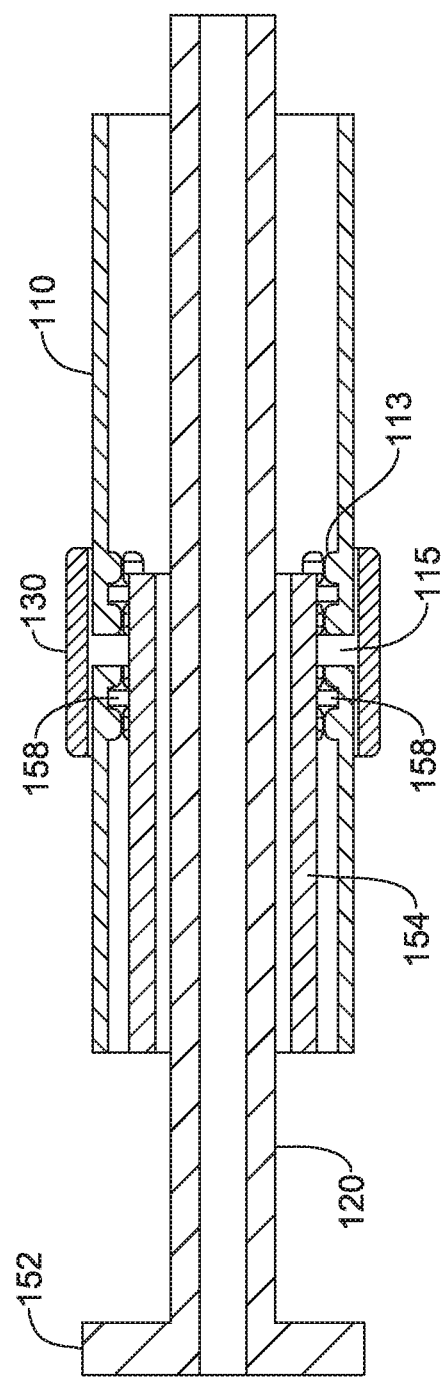
FIG. 5 is a longitudinal cross-sectional view of the handle assembly with the inner member in a proximal position.
Figure 6:
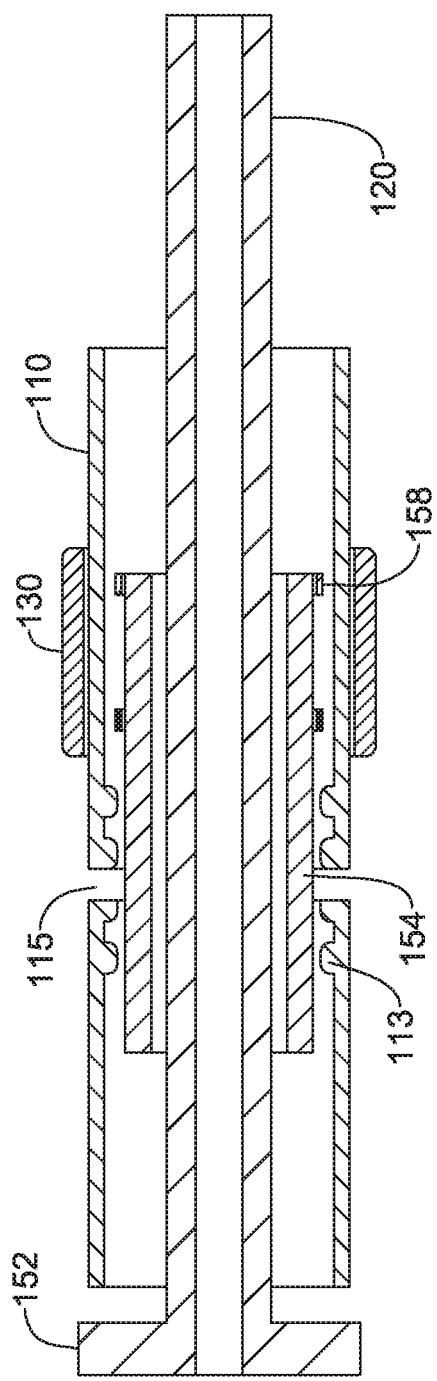
FIG. 6 is a longitudinal cross-sectional view of the handle assembly with the inner member in a distal position.

The projections 158 may be sized to fit between two spaced apart rings of bumps 113 projecting from the inner surface of the outer sheath 110, as shown in FIGS. 4 and 5. As shown in FIG. 4, the bumps 113 may extend circumferentially around the inner surface of the outer sheath 110. The bumps 113 may be spaced apart from one another circumferentially by a distance sufficient for the projections 158 to pass between adjacent bumps 113 when the coupler 154 is rotated to place the projections 158 between bumps 113, and the inner member 120 with attached coupler 154 is moved distally, as shown in the difference between FIGS. 5 and 6. In some instances, a mark 134, such as a dot, circle, line, arrow, or other marking, may be provided on the outer surface of the handle 130, indicating the rotated positions in which the handle 130 and attached inner member 120 may be advanced distally. The marked positions are those in which the projections 158 on the coupler 154 are positioned between adjacent bumps 113. A different marking 136 may be provided to indicate the start of a 360 degree rotation.

FIG. 5 shows the inner member 120 and attached coupler 154 and handle 130 in the proximal-most position, with the projections 158 disposed between circumferential rings of bumps 113 and axially adjacent to bumps 113. In this position, the handle 130, coupler 154, and inner member 120 are rotatable relative to the outer sheath 110, but are prevented from moving axially relative to the outer sheath 110 because the projections 158 are disposed axially adjacent the bumps 113. When the handle 130 is rotated to a position in which the projections 158 are disposed between circumferentially adjacent bumps 113, the handle 130 may then be moved distally, into the position shown in FIG. 6.

Figure 7:
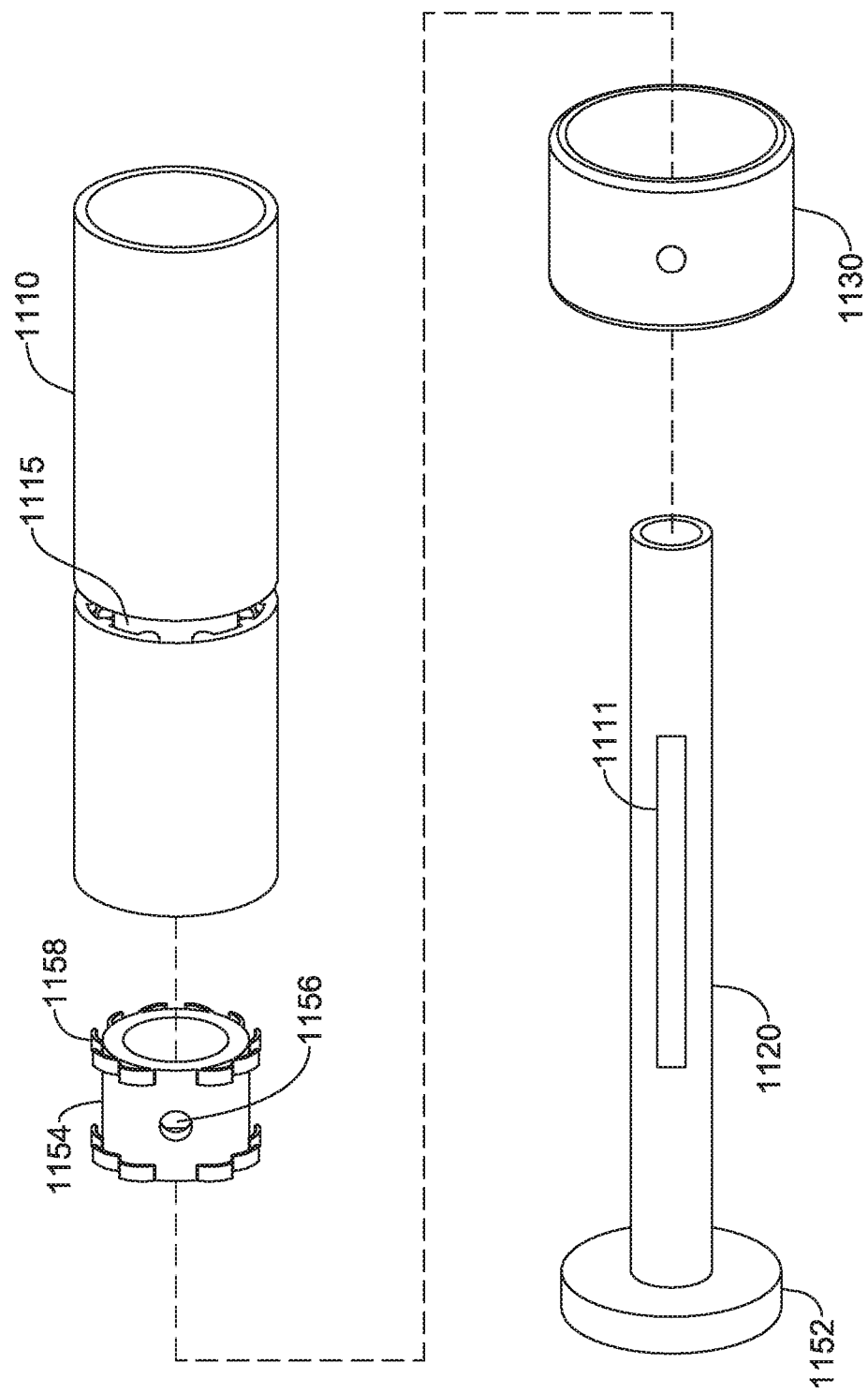
FIG. 7 is an exploded perspective view of another handle assembly.

FIG. 7 shows an alternative handle assembly, in which a channel 1111 is disposed longitudinally along the inner member 1120 and the outer sheath 1110 has only a circumferential slot 1115. The handle assembly includes a handle 1130 with a pin (not shown) that extends through the circumferential slot 1115 in the outer sheath 1110, through the opening 1156 in the coupler 1154. The pin slides along the longitudinal channel 1111 in the inner member 1120, providing the axial movement of the inner member 1120 relative to the outer sheath 1110. The outer sheath 1110 may have a proximal knob 1152, and the coupler 154 may have projections 1158 that slide along the inner surface of the outer sheath 1110. Rotational movement of the inner member 1120 relative to the outer sheath 1110 is provided by the pin connected to the handle 1130 moving through the circumferential slot 1115. In this example, the handle 1130 and coupler 1154 move rotationally, but do not move axially relative to the outer sheath 1110. Axial movement is provided by moving the inner member 1120, with the pin connected to the handle 1130 sliding along the channel 1111.

Figure 8:
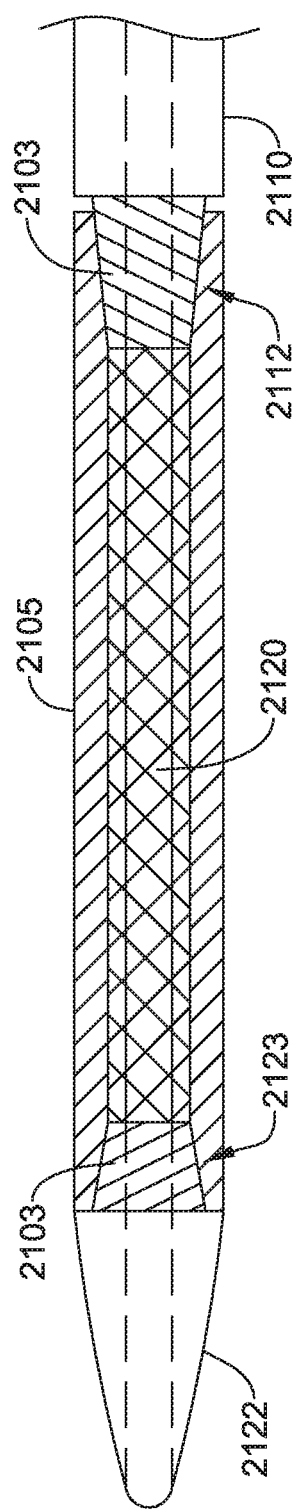
FIG. 8 is a side cross-sectional view of the distal portion of a stent delivery system in accordance with another embodiment of the disclosure.

The threaded proximal end 123 of the distal tip 122 and the threaded distal end 112 of the outer sheath 110 may be substantially cylindrical in shape, as shown in FIG. 1. Alternatively, the threaded proximal end 2123 of the distal tip 2122 on the inner member 2120 and the threaded distal end 2112 of the outer sheath 2110 may both be tapered, with corresponding tapered threaded ends 2103 on each end of the stent sheath 2105, as shown in FIG. 8. It is noted that the threaded proximal end 2123 of the distal tip 2122 and the threaded distal end 2112 of the outer sheath 2110 are illustrated as male threaded portions (i.e., external threading), mating with female threaded portions (i.e., internal threading) of the tapered threaded ends 2103 of the stent sheath 2105. However, in other embodiments the male and female threading of one or both of the junctions may be reversed, if desired. The tapered threaded ends provide for a quick release and reconnection between the threaded distal tip 2122 or outer sheath 2110 and the stent sheath 2105 at the junctions. A reduced number of threads may also be used to provide for quick release. For example, a tapered threaded end and/or reduced thread number may provide a device in which the inner member 2120 or outer sheath 2110 may need to be turned one revolution (360 degrees) or less to fully engage or disengage the threaded connection. In some examples, three-fourths of a turn (270 degrees) or less, one-half of a turn (180 degrees) or less, one-fourth of a turn (90 degrees) or less, or less may be needed to fully engage or disengage the threaded connection.

The inner member 120 may include at least one stent receiving region 126 located along a distal region of the inner member 120 proximal of the distal tip 122. A stent 200 may be disposed over and surround the inner member 120 in the stent receiving region 126, such that the inner member 120 extends through the stent 200 and the stent sheath 105 surrounds the stent 200. The stent 200 may be a self-expanding stent, configured to automatically expand to an expanded state from a constrained state when the stent sheath 105 is removed from the stent. The stent 200 may be made from self-expanding or shape memory alloys such as nitinol, spring steels, resilient polymer, or other materials known in the art for making self-expanding stents. The stent sheath 105 may hold the self-expanding stent 200 in its reduced diameter delivery configuration on the stent receiving region 126 until the stent sheath 105 is moved to uncover the stent 200. In other examples, the stent 200 may be manually expanded.

The stent 200 may have one or more markers (not shown) such as radiopaque markers, disposed on the distal end 210, proximal end 220, or both ends. When markers are present on both the proximal and distal ends 220, 210 of the stent 200, the markers may be the same or different. Additionally, alignment markers (not shown) may be disposed on the outer sheath 110 and/or the inner member 120 to show rotational orientation and/or torqueing of the elements relative to each other. The alignment markers may be radiopaque and may be placed at any location along the length of the device, as desired.

Once either the distal junction 140 or the proximal junction 145 is decoupled (e.g., unscrewed or unthreaded), the stent 200 may be uncovered by or deployed from the stent sheath 105 by moving the distal tip 122 and the outer sheath 110 longitudinally away from each other. This longitudinal movement may be achieved by either holding the outer sheath 110 stationary and advancing the inner member 120 distally and/or holding the inner member 120 stationary and retracting the outer sheath 110 proximally.

Figure 9:
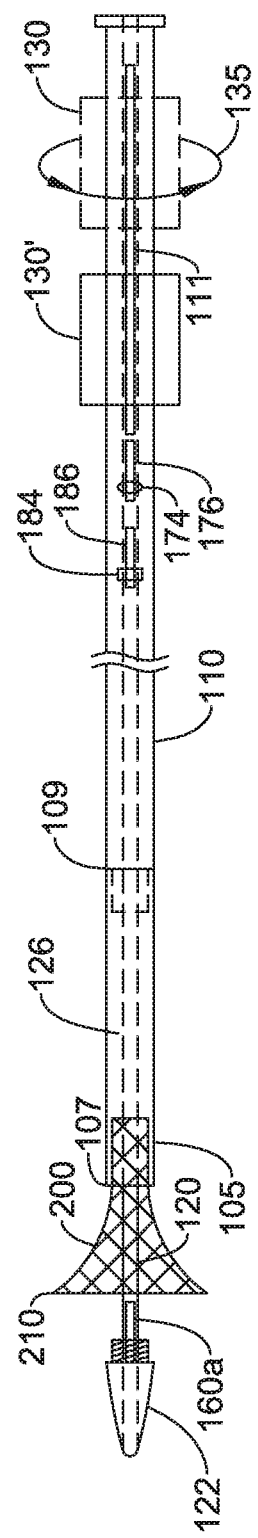
FIG. 9 is a top plan view of a stent delivery system in a distal-to-proximal release state.

A stent 200 may be deployed in a distal-to-proximal direction by decoupling (e.g., unscrewing or unthreading) the distal tip 122 from the stent sheath 105 at the distal junction 140 and then withdrawing the outer sheath 110 (along with the stent sheath 105) proximally, as shown in FIG. 9. Alternatively, the inner member 120 may be advanced distally, exposing the stent 200 from the distal end of the stent sheath 105. The handle 130 may be rotated clockwise to rotate the distal tip 122 clockwise, as indicated by arrow 135 to decouple (e.g., unscrew or unthread) the distal junction 140. Once the distal tip 122 is separated from the distal end 107 of the stent sheath 105, the outer sheath 110 and the stent sheath 105 may be withdrawn proximally while the handle 130 is held stationary. The handle 130 may slide along the longitudinal channel 111 to position 130'. As the stent sheath 105 moves proximally away from the distal tip 122, the distal end 210 of the stent 200 may be initially uncovered and the stent 200 may expand in a distal-to-proximal direction. Once the stent 200 is fully uncovered and fully expanded, the inner member 120 and distal tip 122 may be retracted proximally through the expanded stent 200, coupled (e.g., screwed or threaded) back onto the stent sheath 105, and the device 100 may be removed from the patient leaving the stent 200 in place.

The handle 130 is rotatable relative to the outer sheath 110, to provide rotational motion for the inner member 120 and the distal tip 122. The inner member 120 may be advanced and retracted longitudinally relative to the outer sheath 110 by moving the handle 130 along a longitudinal channel 111 in the outer sheath 110 and/or handle assembly 150. A portion of the handle 130 extends through the longitudinal channel 111 and is attached to the inner member 120. The length of the longitudinal channel 111 may be sufficient to allow the handle 130 to be moved longitudinally to a position where the distal tip 122 is separated from the distal end 107 of the stent sheath 105 by a distance greater than the length of the stent 200.

Figure 10:
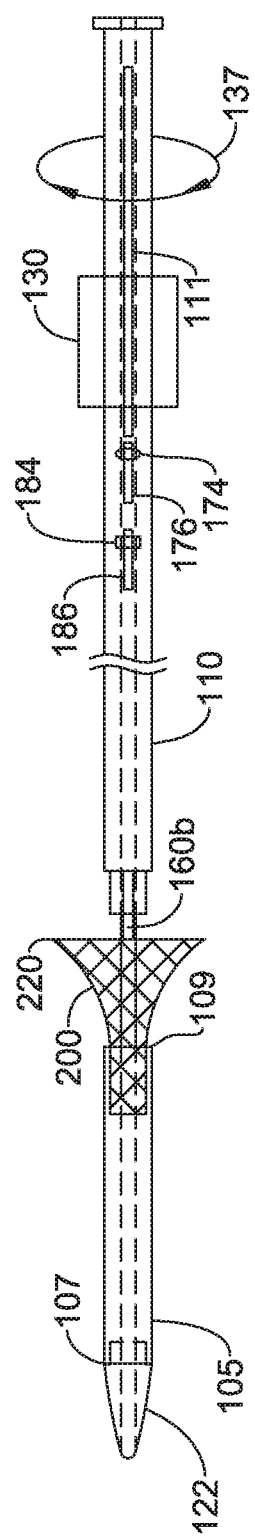
FIG. 10 is a top plan view of a stent delivery system in a proximal-to-distal release state.

A stent 200 may be deployed in a proximal-to-distal direction by decoupling (e.g., unscrewing or unthreading) the outer sheath 110 from the stent sheath 105 at the proximal junction 145 and then the inner member 120 (along with the stent sheath 105) may be advanced distally relative to the outer sheath 110, as shown in FIG. 10. Alternatively, the outer sheath 110 may be withdrawn proximally, exposing the stent 200 from the proximal end of the stent sheath 105. The handle 130 may be rotated counter-clockwise to rotate the stent sheath 105 counter-clockwise, as indicated by arrow 137 to decouple (e.g., unscrew or unthread) the proximal junction 145. Once the outer sheath 110 is separated from the proximal end 109 of the stent sheath 105, the inner member 120 and attached stent sheath 105 may be moved distally, with the handle 130 moving along the longitudinal channel 111, allowing the outer sheath 110 to remain stationary. Alternatively, the outer sheath 110 may be moved proximally. As the stent sheath 105 moves distally away from the outer sheath 110, the proximal end 220 of the stent 200 may be initially uncovered and the stent 200 may expand in a proximal-to-distal direction. Once the stent 200 is fully uncovered and fully expanded, the inner member 120, the distal tip 122, and the stent sheath 105 may be retracted proximally through the expanded stent 200, coupled (e.g., screwed or threaded) back onto the outer sheath 110, and the device 100 removed from the patient leaving the stent 200 in place.

Figure 11:
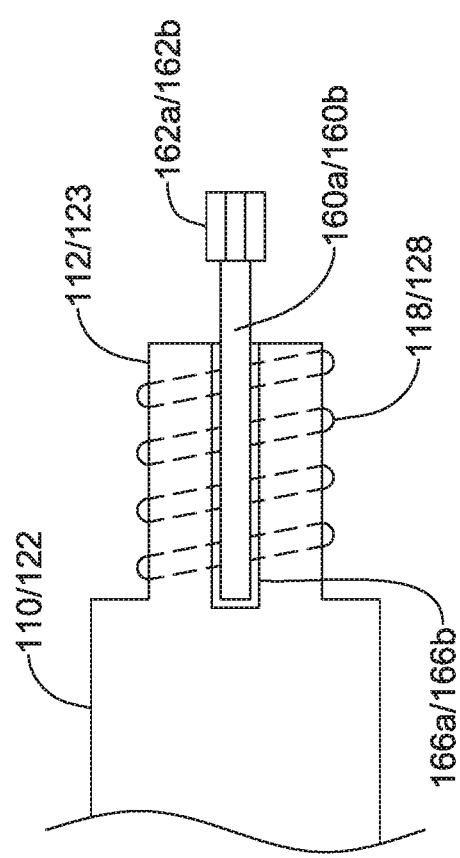
FIG. 11 is a top plan view of either the distal end of the outer shaft and the proximal end of the distal tip of an exemplary stent delivery system.
Figure 12:
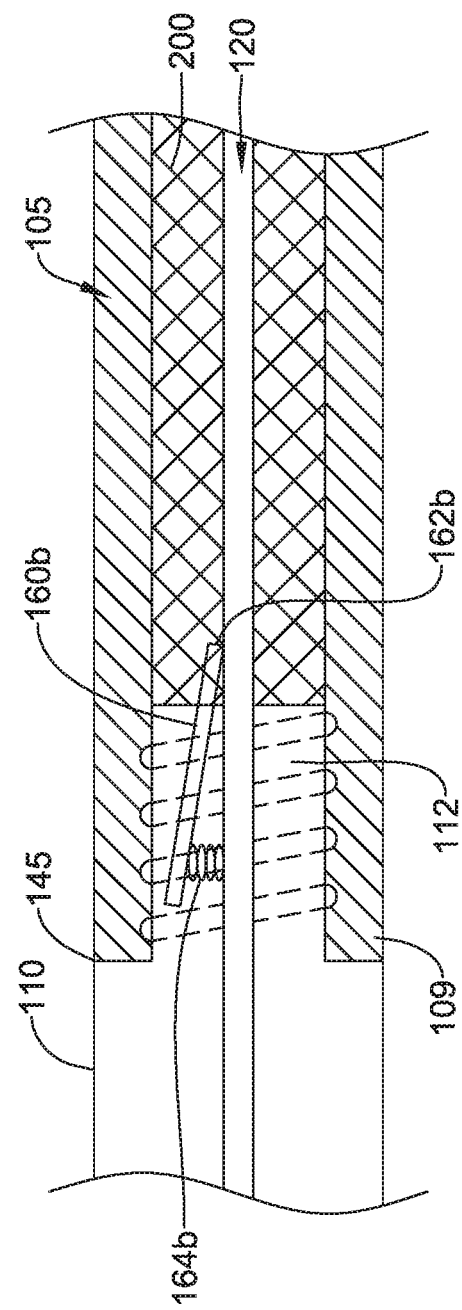
FIG. 12 is a cross-sectional view of the proximal junction between the distal end of the outer shaft and proximal end of the stent sheath of an exemplary stent delivery system.
Figure 13:
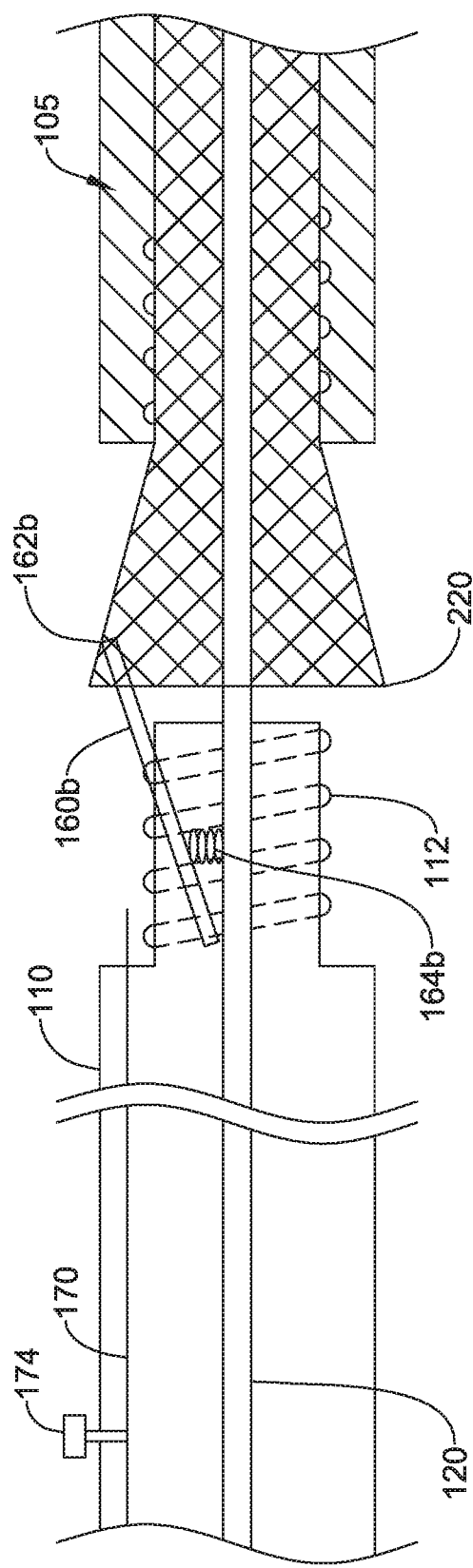
FIG. 13 is a side cross-sectional view of the device in FIG. 12 with the stent sheath partially removed and the proximal end of the stent partially expanded.

The stent 200 may be self-expandable or it may be manually expanded with a device such as a balloon (not shown). In some instances, a stent expander 160a (shown in FIG. 14) may be provided on the proximal end 123 of the distal tip 122 and/or a stent expander 160b (shown in FIG. 12) may be provided on the distal end 112 of the outer sheath 110. FIG. 11 illustrates features of the stent expander 160a/160b. The stent expander 160a/160b may include an elongate member attached at one end in a channel or groove 166a cut in the threaded distal end 112 of the outer sheath 110 and/or a channel or groove 166b cut in the threaded proximal end 123 of the distal dip 122. A second, free end of the stent expander 160a/160b may include an enlarged tip 162a/162b which may be used to adjust the position of the stent 200 upon expansion. A spring 164b may be disposed under the stent expander 160b in the groove 166b, which biases the stent expander 160b in the elevated, radially outward position, as shown in FIG. 13. In other embodiments, the stent expander 160b may be formed of a resilient material, with the stent expander 160b biased to the elevated, radially outward position. FIGS. 12 and 13 illustrate the actuation of the stent expander 160b attached to the distal end 112 of the outer sheath 110. It is noted that the stent expander 160a attached to the proximal end 123 of the distal tip 122 may be configured similarly. When the stent sheath 105 is disposed over the stent 200, as shown in FIG. 12, the stent sheath 105 presses the stent expander 160b down into the groove 166b, compressing the spring 164b so the stent expander 160b does not interfere with the threaded connection between the stent sheath 105 and the distal end 112 of the outer sheath 110. When the stent sheath 105 is advanced distally from the stent 200, the spring 164b expands, returning the stent expander 160b to its biased elevated position and the tip 162b, which may contact an inner surface of the proximal end region of the stent 200 and exerts a radially outwardly directed force on the stent 200, aids the stent 200 in expanding in a proximal-first direction, as shown in FIG. 13. In other instances, the resiliency of the stent expander 160b may cause the stent expander 160b to revert back towards the elevated positioned once unconstrained by the stent sheath 105. The stent expander 160b may aid in expanding the stent 200, whether the stent 200 is self-expanding or manually expanded. Further, the tip 162b of the stent expander 160b may be used to move the fully expanded stent 200 if adjustment to the final position of the stent 200 is desired. In some instances, the tip 162b of the stent expander 160b may contact an inner surface of the stent 200 as the stent sheath 105 is moved longitudinally relative to the stent 200 to facilitate deployment of the stent 200 from the stent sheath 105.

Once the stent 200 is fully expanded, the stent expander 160b must be returned to the collapsed position within the groove 166b. For the stent expander 160b attached to the distal end 112 of the outer sheath 110, this may be accomplished by moving an outer sheath slider 170 distally over the stent expander 160b (e.g., along a radially outward surface of the stent expander 160b), which may push the stent expander 160b radially inward down into the groove 166b. In FIG. 13, the outer sheath slider 170 is in the retracted position, with the distal end of the outer sheath slider 170 just proximal of the stent expander 160b. A handle 174 or other actuator that extends through the outer sheath 110 may be connected to the proximal end of the outer sheath slider 170, and configured to be advanced distally to move the outer sheath slider 170 distally along the stent expander 160b. The outer sheath slider 170 may be a substantially flat, thin element sufficiently rigid to force the stent expander 160b down into the groove 166b. The outer sheath slider 170 may move within a lumen in the outer sheath 110. A channel 176 through the wall of the outer sheath 110 and/or the handle assembly 150 wall may allow the handle 174 to move back and forth longitudinally to actuate the outer sheath slider 170.

Figure 14:
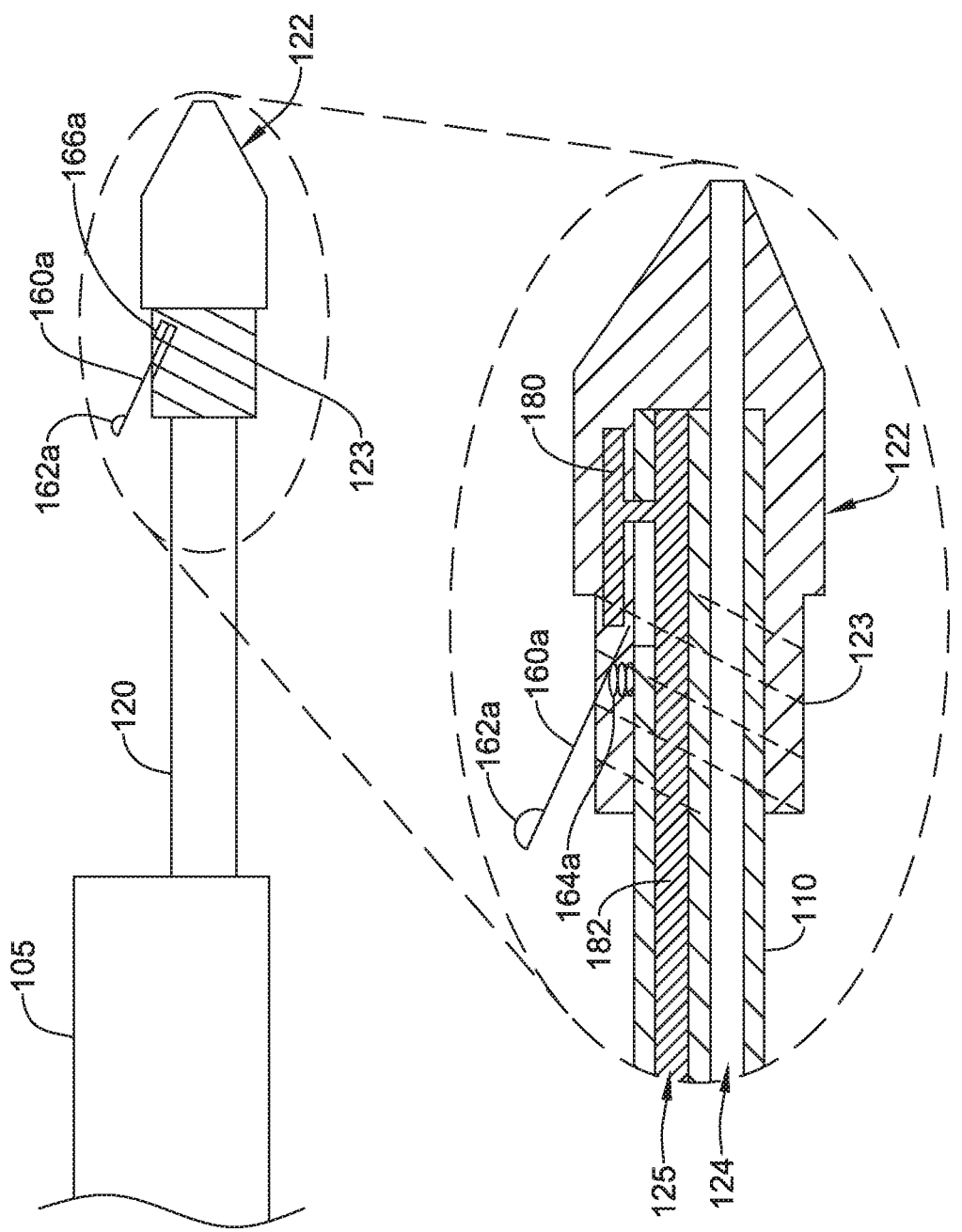
FIG. 14 is a side view of the distal portion of a stent delivery system with a close-up side cross-sectional view of the distal tip.

FIG. 14 shows the stent expander 160a attached to the proximal end 123 of the distal tip 122. The inner member 120 is shown extended distally away from the stent sheath 105. The stent 200 has been removed for clarity. As on the distal end 112 of the outer sheath 110, the stent expander 160a may be attached at one end in a channel or groove 166a cut in the threaded proximal end 123 of the distal tip 122 with a spring 164a under the stent expander 160a. The spring 164a may bias the stent expander 160a in an elevated, radially outward position, as shown in FIG. 14. In other embodiments, the stent expander 160a may be formed of a resilient material, with the stent expander 160a biased to the elevated, radially outward position. An enlarged tip 162a may be attached to or otherwise provided at the free end of the stent expander 160a. As shown in the enlarged cross-sectional view of the distal tip 122 in FIG. 14, an inner member slider 180 is disposed within the distal tip 122. The inner member slider 180 may be attached to a slider extension 182 that is disposed within a second lumen 125 in the inner member 120, adjacent the guidewire lumen 124. Alternatively, the slider extension 182 may be disposed within the guidewire lumen 124. The proximal end of the slider extension 182 may be attached to a handle 184 (shown in FIG. 15) or other actuator that extends through a channel 186 in the outer sheath 110 and/or the handle assembly 150. When the handle 184 is in the distal most position, the inner member slider 180 is distal of the stent expander 160a, as shown in FIG. 14, and the stent expander 160a is in the elevated position. When the handle 184 is moved proximally, the inner member slider 180 may be moved proximally over the stent expander 160a (e.g., along a radially outward surface of the stent expander 160a), pushing the stent expander 160a down into the groove 166a. As with the outer sheath slider 170 on the outer sheath 110, the inner member slider 180 and slider extension 182 on the distal tip 122 may be a substantially flat, thin element sufficiently rigid to force the stent expander 160a down into the groove 166a on the proximal end 123 of the distal tip 122.

During distal-first expansion of the stent 200, as shown in FIG. 9, when the stent sheath 105 is withdrawn proximally from the stent 200, the spring 164a expands, returning the stent expander 160a to its biased elevated position and the tip 162a, which may contact an inner surface of the distal end region of the stent 200 and exerts a radially outwardly directed force on the stent 200, aids the stent 200 in expanding in a distal-first direction. In other instances, the resiliency of the stent expander 160a may cause the stent expander 160a to revert back towards the elevated positioned once unconstrained by the stent sheath 105. The stent expander 160a may aid in expanding the stent 200, whether the stent 200 is self-expanding or manually expanded. Further, the tip 162a of the stent expander 160a may be used to move the fully expanded stent 200 if adjustment to the final position of the stent 200 is desired.

As shown in FIG. 9, the handle 174 connected to the outer sheath slider 170 is positioned near the distal end of the channel 176, indicating the outer sheath slider 170 is positioned distally over the stent expander 160*b* and pressing the stent expander 160*b* into the groove 166*b*, thereby allowing the stent sheath 105 to slide off the proximal end of the stent 200. The handle 184 connected to the inner member slider 180 is also positioned near the distal end of the channel 186, indicating the inner member slider 180 is withdrawn distally of the stent expander 160*a*, allowing the stent expander 160*a* to be in the elevated position, as shown in FIG. 14. The stent expander 160*a* is thus in position to aid the stent 200 in expanding in a distal-to-proximal direction. Once the stent 200 is fully expanded, the handle 184 may be moved proximally along the channel 186, moving the inner member slider 180 proximally over and pressing the stent expander 160*a* into the groove 166*a*. With the stent expander 160*a* in the compressed position, the distal tip 122 may be withdrawn proximally through the expanded stent 200. The distal tip 122 may then be coupled (e.g., screwed or threaded) back onto the distal end of the stent sheath 105 and the entire device may be withdrawn.

During proximal-to-distal expansion of the stent 200, as shown in FIG. 10, when the distal tip 122 and attached stent sheath 105 are advanced distally from the outer sheath 110, the spring 164*b* may expand, returning the stent expander 160*b* to its biased elevated position and the tip 162*b*, which may contact an inner surface of the proximal end region of the stent 200 and exerts a radially outwardly directed force on the stent 200, aids the stent 200 in expanding in a proximal-first direction. In other instances, the resiliency of the stent expander 160*b* may cause the stent expander 160*b* to revert back towards the elevated positioned once unconstrained by the stent sheath 105. The stent expander 160*b* may aid in expanding the stent 200, whether the stent 200 is self-expanding or manually expanded. Further, the tip 162*b* of the stent expander 160*b* may be used to move the fully expanded stent 200 if adjustment to the final position of the stent 200 is desired.

As shown in FIG. 10, the handle 174 connected to the outer sheath slider 170 is positioned near the proximal end of the channel 176, indicating the outer sheath slider 170 is withdrawn proximally of the stent expander 160*b*, allowing the stent expander 160*b* to be in the elevated position, as shown in FIG. 13. The stent expander 160*b* is thus in position to aid the stent 200 in expanding in a proximal-to-distal direction. The handle 184 connected to the inner member slider 180 is also positioned near the proximal end of the channel 186, indicating the inner member slider 180 is positioned proximally over the stent expander 160*a* and pressing the stent expander 160*a* into the groove 166*a*, thereby allowing the stent sheath 105 to slide off the distal end of the stent 200.

Once the stent 200 is fully expanded, the handle 174 may be moved distally along the channel 176, moving the outer sheath slider 170 distally over and pressing the stent expander 160*b* into the groove 166*b*. With the stent expander 160*b* in the compressed position, the distal tip 122 and attached stent sheath 105 may be withdrawn proximally through the expanded stent 200. The distal tip 122 may then be coupled (e.g., screwed or threaded) back onto the distal end of the stent sheath 105 and the entire device may be withdrawn.

Figure 15:
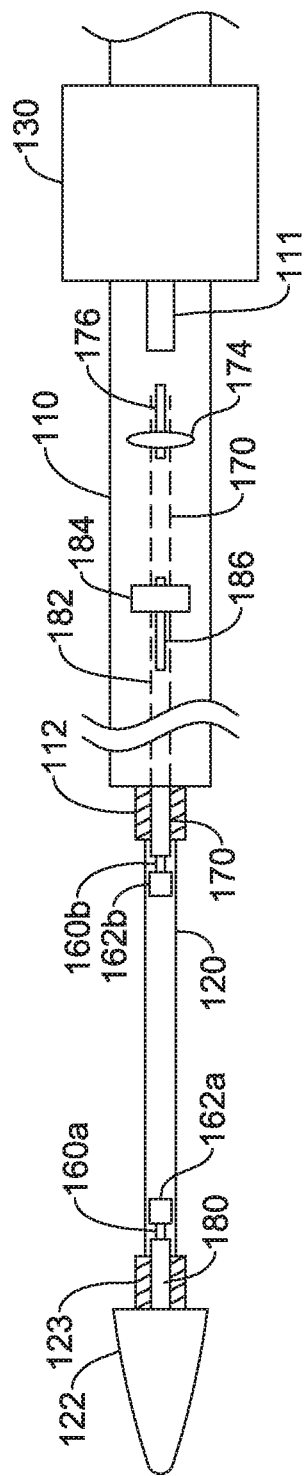
FIG. 15 is a top plan view of the inner member and outer sheath of the stent delivery system.

FIG. 15 is a top view of the outer sheath 110 and inner member 120, but with the stent sheath 105 and stent 200 removed for clarity. Both the outer sheath slider 170 and inner member slider 180 are extended over their respective stent expanders 160*b*/160*a*, forcing the stent expanders 160*b*/160*a* into their respective grooves 166*b*/166*a*. This is indicated by the position of handles 174 and 184. Handle 174, connected to the outer sheath slider 170, is positioned near the distal end of the channel 176, indicating the outer sheath slider 170 is extended distally over the stent expander 160*b* on the distal end 112 of the outer sheath 110. Handle 184, connected to the inner member slider extension 182, is near the proximal end of the channel 186, indicating the inner member slider 180 is extended proximally over the stent expander 160*a* on the proximal end 123 of the distal tip 122. The device, with a stent 200 loaded therein, may be advanced to a target location in a patient in such a configuration. In other instances, the device, with a stent 200 loaded therein, may be advanced to a target location in a patient, with the handles in the opposite positions such that the stent expander 160*a* and the stent expander 160*b* are pressed radially outward against an inner surface of the stent 200. When the device is at the desired location, the user decides whether to deploy the stent 200 in the proximal-to-distal or distal-to-proximal direction, and thereafter actuate either the handle 174 or the handle 184 to facilitate deployment of the stent 200.

The materials that can be used for the various components of the delivery device 100 (and/or other devices disclosed herein) and the various tubular members disclosed herein may include those commonly associated with medical devices. For simplicity purposes, the following discussion makes reference to outer sheath 110 and inner member 120 and other components of device 100. However, this is not intended to limit the devices and methods described herein, as the discussion may be applied to other similar devices and/or components of devices or devices disclosed herein.

The various components of the devices/systems disclosed herein may include a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In at least some embodiments, portions or all of the delivery device 100 and/or other components of delivery system may be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 100 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the delivery device 100 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent delivery system comprising:
an elongated inner member extending between a distal tip and a proximal end;
a stent surrounding a stent receiving region of the elongated inner member, the stent having a collapsed configuration and an expanded configuration;
an elongated outer sheath slidably disposed over the inner member, the outer sheath extending between a distal end and a proximal end,
a stent sheath surrounding the stent to restrain the stent in the collapsed configuration;
a proximal junction detachably coupling the distal end of the outer sheath to a proximal end of the stent sheath, the proximal junction being actuatable to selectively uncouple the distal end of the outer sheath from the proximal end of the stent sheath;
a distal junction detachably coupling a distal end of the stent sheath to the distal tip of the inner member, the distal junction being actuatable to selectively uncouple the stent sheath from the distal tip;
wherein the proximal junction is actuatable by rotating the inner member relative to the outer sheath in a first direction, and the distal junction is actuatable by rotating the inner member relative to the outer sheath in a second direction that is opposite the first direction; and
at least a first stent expanding element disposed at at least one of the distal tip or the distal end of the outer sheath, the first stent expanding element having a radially retracted position and a radially elevated position.

2. The stent delivery system of claim 1, wherein the distal tip includes a proximally extending threaded element, the distal end of the outer sheath includes a distally extending threaded element, and the stent sheath includes threaded cavities on the distal and proximal ends thereof, the threaded cavities configured to receive the proximally and distally extending threaded elements.

3. The stent delivery system of claim 2, wherein the distally and proximally extending threaded elements are tapered.

4. The stent delivery system of claim 3, wherein the distal and proximal threaded connections are each fully coupled and uncoupled by less than a 360 degree turn.

5. The stent delivery system of claim 2, wherein the first stent expanding element includes a first elongated member having a first end attached to the proximally extending threaded element on the distal tip or to the distally extending threaded element on the distal end of the outer sheath, the first stent expanding element having a second free end opposite the first end.

6. The stent delivery system of claim 5, further comprising a first spring biasing the first stent expanding element in the elevated position.

7. The stent delivery system of claim 6, wherein the first spring is disposed in a first groove extending longitudinally through the threading on the threaded element to which the first elongated member is attached, wherein the first elongated member is disposed within the first groove when the first stent expanding element is in the retracted position.

8. The stent delivery system of claim 7, further comprising a first slider element extending from a proximal region of the outer sheath to a distal end positioned adjacent the first end of the first elongated member, the first slider element configured to slide over a portion of the first elongated member, moving the first stent expanding element from the elevated position to the retracted position.

9. The stent delivery system of claim 8, wherein the first stent expanding element is disposed on the distal tip, the system further comprising:
a second stent expanding element disposed at the distal end of the outer sheath, the second stent expanding element including a second elongated member having a first end attached to the distally extending threaded element on the distal end of the outer sheath and a second free end opposite its first end, the second stent expanding element having a radially retracted position and a radially elevated position; and
a second slider element extending from a proximal region of the outer sheath to a distal end positioned adjacent the first end of the second elongated member, the second slider element configured to slide over a portion of the second elongated member, moving the second stent expanding element from the elevated position to the retracted position.

10. The stent delivery system of claim 9, wherein the first and second sliders are independently moveable.

11. The stent delivery system of claim 1, wherein the first stent expanding element is disposed on the distal tip, the system further comprising a second stent expanding element disposed on the distal end of the outer sheath.

12. The stent delivery system of claim 11, wherein the first stent expanding element has a free end extending proximally and the second stent expanding element has a free end extending distally.

13. The stent delivery system of claim 1, wherein the stent is deployable in a proximal-to-distal manner by uncoupling the proximal junction and moving the distal tip and stent sheath distally together relative to the stent.

14. The stent delivery system of claim 1, wherein the stent is deployable in a distal-to-proximal manner by uncoupling the distal junction and moving the stent sheath and outer sheath proximally together relative to the stent.

15. A method of selectively deploying a stent in a proximal-to-distal manner or in a distal-to-proximal manner, comprising:
    advancing a stent delivery system to a target location, the stent delivery system including an elongated inner member extending between a distal tip and a proximal end, a stent surrounding a stent receiving region of the elongated inner member and having a collapsed configuration and an expanded configuration, an elongated outer sheath slidably disposed over the inner member and extending between a distal end and a proximal end, a stent sheath surrounding the stent and removably coupled to the distal tip of the inner member and the distal end of the outer sheath, a first stent expanding element disposed at the distal tip, and a second stent expanding element disposed at the distal end of the outer sheath, the first and second stent expanding elements having a retracted position and an elevated position, the first and second stent expanding elements being biased in the elevated position;
    deploying the stent in a distal-to-proximal manner by:
        rotating the inner member relative to the outer sheath in a first rotational direction, to selectively decouple a distal end of the stent sheath from the distal tip; and
        moving the stent sheath coupled to the outer sheath proximally relative to the stent to uncover the stent, wherein moving the stent sheath proximally away from the distal tip causes the first stent expanding element to return to the biased elevated position and hold the stent as the stent sheath is moved proximally away from the stent; or
    deploying the stent in a proximal-to-distal manner by:
        rotating the inner member relative to the outer sheath in a second rotational direction opposite the first rotational direction to selectively decouple the distal end of the outer sheath from a proximal end of the stent sheath; and
        moving the stent sheath coupled to the distal tip distally relative to the stent to uncover the stent, wherein moving the stent sheath distally away from the distal end of the outer sheath causes the second stent expanding element to return to the biased elevated position and hold the stent as the stent sheath is moved distally away from the stent.

16. A stent delivery system comprising:
    an elongated inner member extending between a distal tip and a proximal end;
    a stent surrounding a stent receiving region of the elongated inner member, the stent having a collapsed configuration and an expanded configuration;
    an elongated outer sheath slidably disposed over the inner member, the outer sheath extending between a distal end and a proximal end,
    a stent sheath surrounding the stent to restrain the stent in the collapsed configuration;
    a proximal junction detachably coupling the distal end of the outer sheath to a proximal end of the stent sheath, the proximal junction being actuatable to selectively uncouple the distal end of the outer sheath from the proximal end of the stent sheath;
    a distal junction detachably coupling a distal end of the stent sheath to the distal tip of the inner member, the distal junction being actuatable to selectively uncouple the stent sheath from the distal tip;
    wherein the proximal junction is actuatable by rotating the inner member relative to the outer sheath in a first direction, and the distal junction is actuatable by rotating the inner member relative to the outer sheath in a second direction that is opposite the first direction; and
    a first stent expanding element disposed at the distal tip and a second stent expanding element disposed at the distal end of the outer sheath, the first and second stent expanding elements each having a radially retracted position and a radially elevated position, wherein the first stent expanding element includes a first elongated member having a first end attached to the distal tip and a second free end, and the second stent expanding element includes a second elongated member having a first end attached to the distal end of the outer sheath and a second free end, wherein the first and second stent expanding elements are each biased in the elevated position.

17. The stent delivery system of claim 16, further comprising:
    a first spring disposed in a first groove extending longitudinally through threading on a threaded element extending proximally from the distal tip, the first spring disposed under the first end of the first elongated member and biasing the first elongated member in the elevated position, wherein the first elongated member is disposed within the first groove when the first stent expanding element is in the retracted position; and
    a second spring disposed in a second groove extending longitudinally through threading on a threaded element extending distally from the distal end of the outer sheath, the second spring disposed under the first end of the second elongated member and biasing the second elongated member in the elevated position, wherein the second elongated member is disposed within the second groove when the second stent expanding element is in the retracted position.

18. The stent delivery system of claim 16, further comprising:
    a first slider element extending from a proximal region of the outer sheath to a distal end positioned adjacent the first end of the first elongated member, the first slider element configured to slide over a portion of the first elongated member, moving the first stent expanding element from the elevated position to the retracted position; and
    a second slider element extending from a proximal region of the outer sheath to a distal end positioned adjacent the first end of the second elongated member, the second slider element configured to slide over a portion of the second elongated member, moving the second stent expanding element from the elevated position to the retracted position.

19. The stent delivery system of claim 18, wherein the first and second sliders are independently moveable.

20. The stent delivery system of claim 16, wherein the distal tip includes a proximally extending threaded element, the distal end of the outer sheath includes a distally extending threaded element, and the stent sheath includes threaded cavities on the distal and proximal ends thereof, the threaded cavities configured to receive the proximally and distally extending threaded elements, wherein the proximally and distally extending threaded elements are each tapered.

\* \* \* \* \*